United States Patent [19]
Valiquette et al.

[11] 4,023,564
[45] May 17, 1977

[54] ARRHYTHMIA DETECTOR

[75] Inventors: Donley J. Valiquette, Camarillo; Tom A. Finger, Tustin, both of Calif.

[73] Assignee: Spacelabs, Inc., Chatsworth, Calif.

[22] Filed: Jan. 26, 1976

[21] Appl. No.: 652,622

[52] U.S. Cl. .......................................... 128/2.06 A
[51] Int. Cl.² .......................................... A61B 5/04
[58] Field of Search ................. 128/2.06 A, 2.06 F, 128/2.06 R

[56] References Cited
UNITED STATES PATENTS

| | | | |
|---|---|---|---|
| 3,524,442 | 8/1970 | Horth | 128/2.06 A |
| 3,616,790 | 11/1971 | Harris | 128/2.06 A |
| 3,759,248 | 9/1973 | Valiquette | 128/2.06 A |
| 3,858,034 | 12/1974 | Anderson | 128/2.06 A |

*Primary Examiner*—William E. Kamm

*Attorney, Agent, or Firm*—Fraser and Bogucki

[57] ABSTRACT

The amplitude of each R wave of an electrocardiogram signal at each of a plurality of sample points is compared with reference values representing amplitudes of a reference template at the sample points, with each new set of R wave amplitudes at the test points being applied to update the reference values by being averaged therewith. The amplitudes of each R wave which has been determined to differ from the reference template at at least one of the test points are stored in a recirculating shift register memory in addition to being compared to other values previously stored in the memory. Whenever a set of amplitudes is determined to be equal to a set of amplitudes previously stored in the memory, an alarm signal is generated to identify an arrhythmia.

6 Claims, 5 Drawing Figures

ARRHYTHMIA DETECTOR

BACKGROUND OF THE INVENTION

1. Field of the Invention

The present invention relates to heart-monitoring devices, and more particularly to devices which analyze the R waves of an electrocardiogram signal to detect arrhythmias of the heart.

2. History of the Prior Art

Various devices are known for monitoring heart function. Such devices typically function by analyzing signals representative of heart function such as an electrocardiogram (ECG) signal.

Detection devices of this type have found a widespread use in conjunction with patients known to have a cardiac problem such as in the case of heart patients in an intensive care unit. Such devices also have many uses outside of the intensive care unit such as in conjunction with persons who are not known to have a cardiac condition as such but who may exhibit suspicious symptoms. For example, a person may have a mild heart attack and not know what it is. However, by the time the person gets to a doctor, the symptoms may have sufficiently subsided so as to make diagnosis difficult. In such situations it would be desirable to be able to monitor the person's heart activity over an extended period of time and outside of the doctor's office. In still other situations, it may be desirable to be able to monitor a person's heart activity over a prolonged period of time to determine whether that person's heart activity is normal and thereby indicate that certain symptoms are psychosomatic or caused by other factors.

A number of different detecting devices are known for monitoring a person's heart activity. Many such devices respond to the reoccurring R wave within the electrocardiogram signal in an attempt to detect improper heart beats or arrhythmias. One of the more common detecting devices of the type which responds to R waves includes what is commonly known as a QRS detector. The QRS detector responds to the beginning of each R wave within an electrocardiogram signal by generating a pulse of fixed width or duration. Further circuitry analyzes the time distance between the generated pulses to make a determination of heart rate or pulse rate. Detecting devices of this type are nothing more than pulse rate monitors and make no attempt to analyze the R waves except in terms of their frequency of occurrence.

Still other detecting devices make some attempt at analyzing various waveform components of the electrocardiogram signal by sensing the zero crossings of such signal. The locations of the zero crossings may then be analyzed such as by comparing their time of occurrence with a reference template representing a desired or normal pattern of zero crossings. The problem with detection devices of this type is that they are highly prone to false triggering in response to noise rather than to valid heart arrhythmias. For example, it is quite easy to respond to and analyze one of the various noise signals commonly generated by the body, thinking it to be the electrocardiogram signal. Still furhter problems stem from the fact that such detection systems typically do not change the reference template or criteria in response to the gradual changes in heart function which occur in everyone. Thus, a reference template which defines normal heart activity for the patient at a given moment may not accurately reflect the same patient's normal heart activity at a later time.

Brief Summary of the Invention

The present invention provides an arrhythmia detector which compares repeating waveform complexes from a patient's electrocardiogram signal with a reference template. The reference template is updated by each new waveform complex so as to change with the patient's changing heart activity. Accordingly, the system is not sensitive to gradual changes in the patient's heart activity over a period of time. To avoid false triggering of an alarm due to waveform complexes which are produced by noise, each waveform complex which is determined to differ from the reference template is next compared with waveform complexes which were previously determined to be different from the reference template. If the waveform complex in question turns out to be equal to any of the stored complexes, only then does the system determine that an arrhythmia is present. Since waveform complexes which are noise produced are usually random and seldom repeat themselves, the comparison of suspicious waveform complexes with those previously so identified and stored greatly minimizes the possibility of false triggering due to noise.

In one preferred arrangement of an arrhythmia detector according to the invention, a conventional QRS detector responds to the beginning of each R wave of an electrocardiogram signal to define six different test or sample points occurring along the length of the R wave at six points in time following the beginning of such wave. At each of the test points, the amplitude of the R wave is compared with a stored value representing the amplitude of a reference template at that particular test point. If the amplitude of the R wave being tested is within a certain range of the reference value, a comparator determines that the R wave being tested fits the template at that particular test point. The amplitude of the R wave is then averaged with the reference value so as to update the reference template. The system sequences through the test points with the amplitude of the R wave at each test point being first compared with the reference template and thereafter averaged with the reference value at that test point. If the amplitudes of the R wave substantially equal the test values at each of the various test points, the R wave is determined to represent normal heart function. If, however, the R wave differs from the reference template at one or more of the test points, the R wave is identified as a potential arrhythmia.

Potential arrhythmias are transferred to a memory where they are stored for subsequent comparison with other potential arrhythmias. Before being stored, however, the potential arrhythmia is compared with stored values representing previously occurring potential arrhythmias. If the potential arrhythmia is determined to equal any one of the previously stored arrhythmias, an alarm signal is generated to denote the occurrence of an arrhythmia.

BRIEF DESCRIPTION OF THE DRAWINGS

The foregoing and other objects, features and advantages of the invention will be apparent from the following more particular description of a preferred embodiment of the invention, as illustrated in the accompanying drawings, in which.

DETAILED DESCRIPTION

Figure 1:
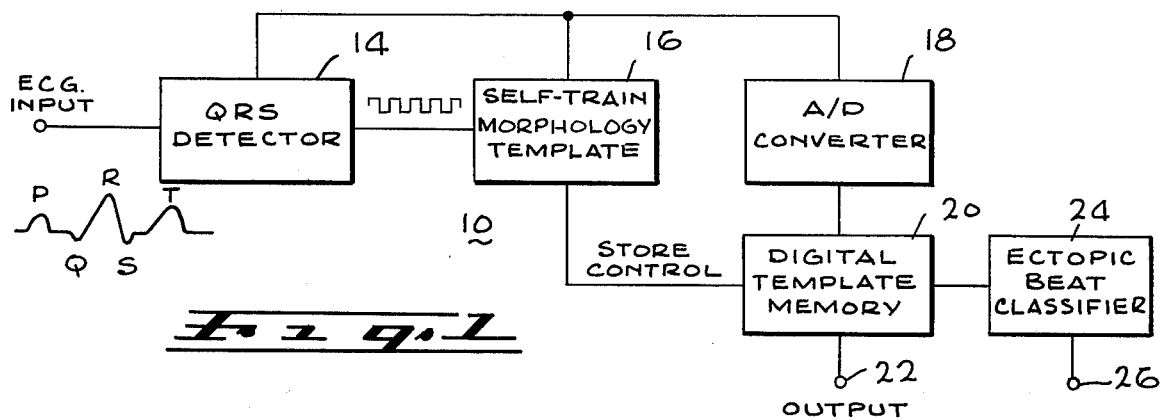
FIG. 1 is a block diagram of an arrhythmia detector in accordance with the invention.

FIG. 1 depicts an arrhythmia detector 10 in accordance with the invention having an input terminal 12 for receiving an electrocardiogram (ECG) signal, a typical waveform of a portion of which signal is shown in FIG. 1 below the input terminal 12. As is well know in the art, the ECG waveform repeats with each heart beat and includes P, Q, R, S and T portions, as well as certain other portions which are not shown. The P portion is produced by the atrium, the R portion or wave is ventricle related, and the T portion relates to depolarization. The Q and S portions respectively denote the beginning and end of the R wave.

As is known in the art, the R wave provides a reliable representation of heart activity. Although the size and shape of the R wave can change gradually as bodily conditions change, the R wave does not change significantly on a beat-to-beat basis in the normal, healthy heart. Where abnormal conditions are present, however, the R wave frequently does change on a beat-to-beat basis or over a relatively short period of time.

In accordance with the invention, R waves which differ significantly from the normal pattern of such waves and which are therefore designated ectopic beats or arrhythmias are used to identify an abnormal heart condition. The present invention does this by first comparing each incoming R wave with a reference template representing the average or normal R wave. R waves which differ from the reference template at at least one of a plurality of test points at which comparisons are made are identified as potential arrhythmias. At the same time, the reference template is continually updated by averaging the various signal values defining the template with the signal values of the incoming R wave at the various test points. In this way the reference template is able to change as the R waves undergo gradual changes over prolonged periods of time. In addition, the reference template is established in response to the incoming R waves rather than by some arbitrary or independent set of values and is therefore always truly representative of the average or normal R waves. R waves which differ significantly from the normal or reference pattern and which therefore denote ectopic beats or arrhythmias have a tendency to reoccur in a pattern over a relatively short period of time. This is not true of noise which is highly erratic and random in its occurrence. Accordingly, valid arrhythmias can be separated from noise by generating an alarm only when it is determined that a particular potential arrhythmia has previously occurred at least once. This is done by comparing each R wave which has been identified as a potential arrhythmia with R waves previously identified as potential arrhythmias. Where a match occurs, an alarm signal is generated. Regardless of whether or not a match occurs, the potential arrhythmia is stored for purposes of subsequent comparison with other R waves identified as potential arrhythmias.

Figure 3:
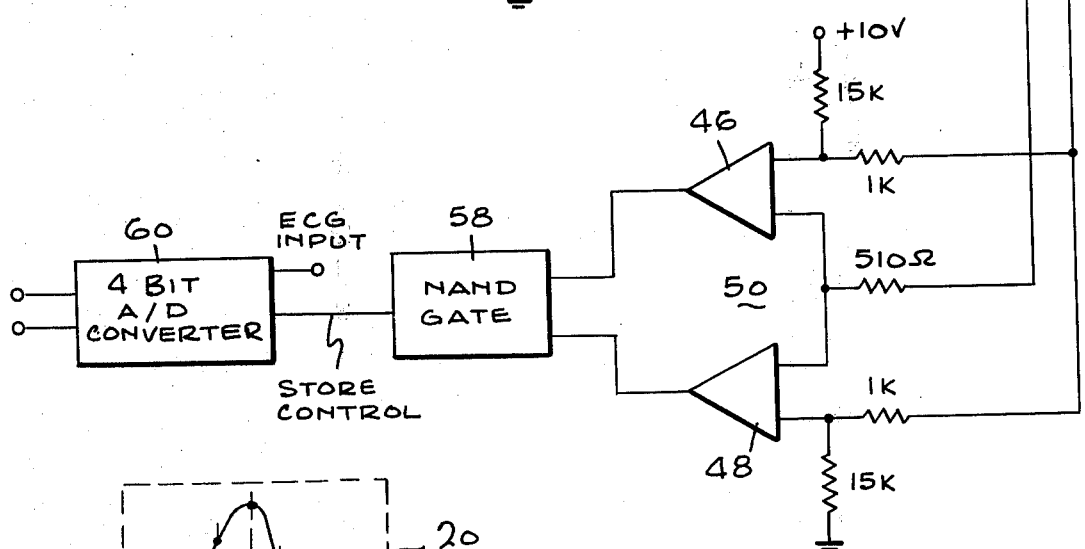
FIG. 3 is a diagramatic plot useful in explaining the operation of the circuitry of FIG. 2.
Figure 3:
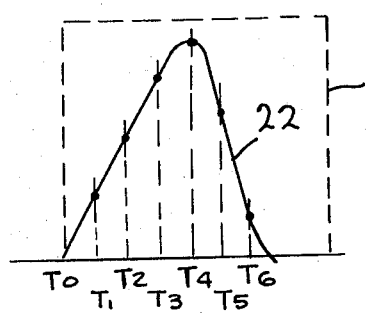

Referring again to FIG. 1, the ECG signal at the input 12 is applied to a QRS detector 14 as well as to a self-train morphology template 16 and an analog to digital converter 18. The QRS detector 14 can comprise any conventional circuit of the type which generates a pulse in response to each R wave of the ECG signal, with one example being 'ECG Cardiotachometer' Model No. 1515, sold by Spacelabs, Inc. of Chatsworth, California. Such circuits typically comprise an R wave filter for separating the R waves from other portions of the ECG waveform and a level detector for determining whether the R waves are valid. Those R waves which are determined to be valid then generate a pulse, typically of fixed duration and having a leading edge coinciding with the beginning of the R wave. One such pulse 20 is shown in FIG. 3 in conjuction with an R wave 22. As seen in FIG. 1, the QRS detector 14 produces at its output a series of pulses, with each pulse being generated in response to and corresponding to a different R wave in the incoming ECG signal.

The ECG signal at the input terminal 12 is applied to the self-train morphology template 16 together with the output pulses from the QRS detector 14. As described hereafter in connection with FIG. 2, the self-train morphology template 16 responds to each pulse from the QRS detector 14 to initiate a timed sampling of the R wave at six different test points. The amplitude of the R wave at each of the test points is compared with the corresponding values of a reference template, with the reference template constantly being updated by averaging the amplitudes of the R wave with the reference values of the template. If the amplitude of the R wave at any one of the test points is determined to differ from the corresponding reference value by more than a predetermined amount, a store control signal is applied to a digital template memory 20 indicating that the R wave has been tagged as a potential arrhythmia.

When an R wave has been tagged as a potential arrhythmia by the generation of a store control signal, the digital equivalents of the amplitude of the R wave at the six different test points as provided by the analog to digital converter 18 are compared with the digital values of other R waves previously tagged as potential arrhythmias and stored within the memory 20. The potential arrhythmia is then stored in the memory 20 for comparison with the digital values of R waves which are subsequently tagged as potential arrhythmias. The storage portion of the memory 20 comprises a recirculating shift register designed to store the digital values of a selected number of R waves. As each new R wave is stored in the memory 20, the values of the oldest R wave stored in the memory are destroyed. In each case where an incoming R wave tagged as a potential arrhythmia proves to be substantially equal to one of the R waves stored in the memory, an alarm signal is provided at an output terminal 22.

An optional feature may be added to the arrhythmia detector 10 of FIG. 1 in the form of an ectopic beat classifier 24. As described hereafter in conjunction with FIG. 5, the beat classifier 24 includes a plurality of register stages for storing R waves. In actual practice, the abnormal heart seldom generates more than a few different abnormal R waves or arrhythmias. The problem, however, is to separate these valid arrhythmias from the multitude of similar signals produced by noise and other phenomenon. The ectopic beat classifier 24 does this by storing only those R waves which are determined by the digital template memory 20 to equal a previously stored R wave. In this way, the beat classifier 24 stores only R waves which have already been determined to be valid arrhythmias. After a few valid arrhythmias are stored in the ectopic beat classifier 24, the digital template memory 20 is no longer needed. Instead, R waves tagged as potential arrhythmias by the self-train morphology template 16 are provided by the analog to digital converter 18 directly to the ectopic beat classifier 24 where they are compared with the valid arrhythmias stored in the classifier 24. A positive comparison produces an alarm signal at an output terminal 26 of the ectopic beat classifier 24. The beat classifier 24 produces other useful data such as by using counters to determine the frequency with which a particular arrhythmia occurs over a given period of time.

Figure 2:
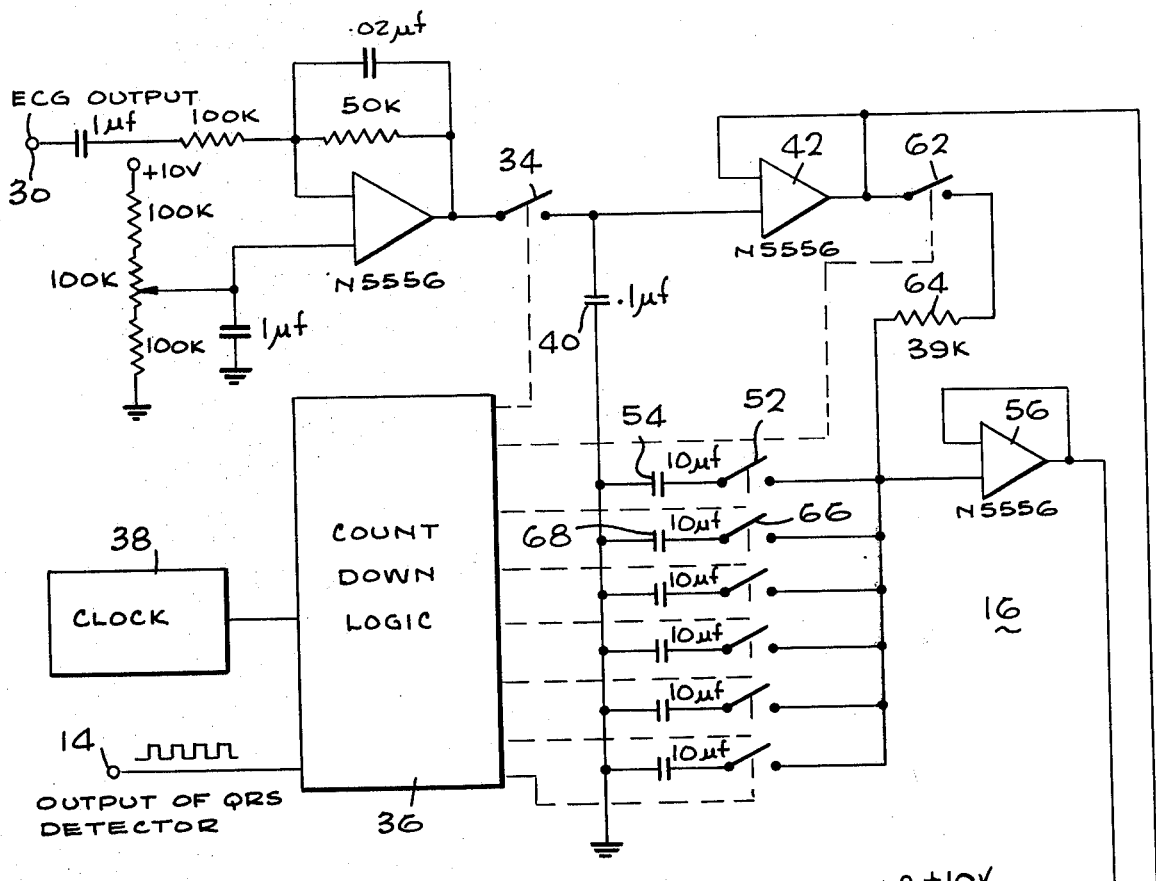
FIG. 2 is a partial block and partial schematic diagram showing the details of the self-train morphology template of the FIG. 1 arrangement.

FIG. 2 shows one preferred circuit for use as the self-train morphology template 16 in the arrangement of FIG. 1. The ECG signal from the input terminal 12 of FIG. 1 is applied to a terminal 30 coupled to a filter and sensitivity threshold 32. The filter and sensitivity threshold 32 which is coupled between the input terminal 30 and a switch 34 effectively changes the gain of the incoming signal by varying the amplitude thereof so as to establish a desired sensitivity threshold for purposes of comparison with the stored values comprising the reference template. The output pulses from the QRS detector 14 are applied to count down logic 36 together with the output of a clock 38. As previously noted, the QRS detector 14 commences generation of a pulse in response to the beginning of each R wave of the ECG signal. Such pulse causes the count down logic 36 to begin a timed sequence of events in response to the clock 38.

Referring to FIG. 3, the beginning of each pulse such as the pulse 20 shown therein indicates the beginning of an R wave such as the wave 22 shown therein at a time $T_0$. Thereafter, the count down logic 36 responds to the clock 38 to define six different test points occurring at times $T_1$, $T_2$, $T_3$, $T_4$, $T_5$, and $T_6$ after the time $T_0$.

At the time $T_1$, as defined by the first cycle of the clock 38 after $T_0$, the count down logic 36 responds by momentarily closing the switch 34 so as to allow a signal corresponding to the amplitude of the R wave 22 and as altered by the filter and sensitivity threshold 32 to charge a capacitor 40. Thereafter, the switch 34 is opened by the count down logic 36 and the level of charge on the capacitor 40 is communicated by an operational amplifier 42 operating as a unity gain buffer amplifier to one input of each of two different operational amplifiers 46 and 48 which comprise a comparator 50. At the same time, a switch 52 is closed by the count down logic 36 to communicate the level of charge stored on a capacitor 54 via an operational amplifier 56 coupled to operate as a unity gain buffer amplifier to a second input of each of the operational amplifiers 46 and 48 within the comparator 50. The level of the charge on the capacitor 54 comprises the first of six different stored values making up the reference template. The comparator 50 determines whether the amplitude of the incoming R wave at the first test point $T_1$ is within a range of values defined by the level of charge on the capacitor 54 ± a fixed amount as determined by the sensitivity setting of the filter and sensitivity threshold 32. Thus, the operational amplifier 46 determines whether the amplitude of the incoming R wave is equal to or no more than a fixed amount greater than the amplitude represented by the level of charge on the capacitor 54. Similarly, the operational amplifier 48 determines whether the incoming R wave amplitude is equal to or no more than a fixed amount less than the amplitude represented by the level of charge on the capacitor 54. A NAND gate 58 coupled to the outputs of the amplifier 46 and 48 provides the store control signal to a 4 bit analog to digital converter 60 when the amplitude of the incoming R wave is determined by the comparator 50 to lie outside of the defined band of values surrounding the reference value from the capacitor 54.

When the comparator 50 has compared the levels of charge on the capacitors 40 and 54, a switch 62 is momentarily closed by the count down logic 36 to couple the capacitor 40 to the capacitor 54 via a resistor 64 and the closed switch 52. The level of charge on the capacitor 54 is changed by an amount corresponding to the difference between the level of charge thereon and the level of charge on the capacitor 40, so as to update the reference value at the first test point $T_1$. Thereafter, the switches 52 and 62 are opened by the count down logic 36.

When the clock 38 reaches its next cycle to designate the second test point $T_2$, the count down logic 36 again closes the switch 34 momentarily so as to charge the capacitor 40 to a value corresponding to the amplitude of the R wave 22 at the second test point $T_2$. The count down logic 36 then closes a switch 66 to enable the comparator 50 to compare the charge on the capacitor 40 with the charge on a capacitor 68 representing the second stored value of the reference template. Again, after the comparison is made, the switch 62 is momentarily closed so as to update the charge on the capacitor 68 in accordance with the charge on the capacitor 40.

The self-train morphology template 16 continues to sequence through each of the test points under the control of the clock 38 and the count down logic 36. As each new test point is reached, the swich 34 is closed and the capacitor 40 is charged. Thereafter, a switch is closed so as to couple one of the capacitors defining the reference template to the comparator 50 for comparison with the charge on the capacitor 40, following which the switch 62 is momentarily closed so as to update the charge on the capacitor.

The count down logic 36 may comprise any appropriate logic circuitry for operating in conjuction with the clock 38 to provide the timed sequence of events described above. One circuit which can be used to accomplish this consists of two-input and three-input NOR gates, inverters, and a one through ten pulse decoding network. In such circuit, the clock-derived pulses are decoded and converted to a phased array of lower frequency pulses which are used to activate the swtiches in the self-train morphology template 16. Commercially available integrated circuits which can be used include those sold by Radio Corporation of America under the designations CD4001, CD4009, CD4017 and CD4025.

Figure 4:
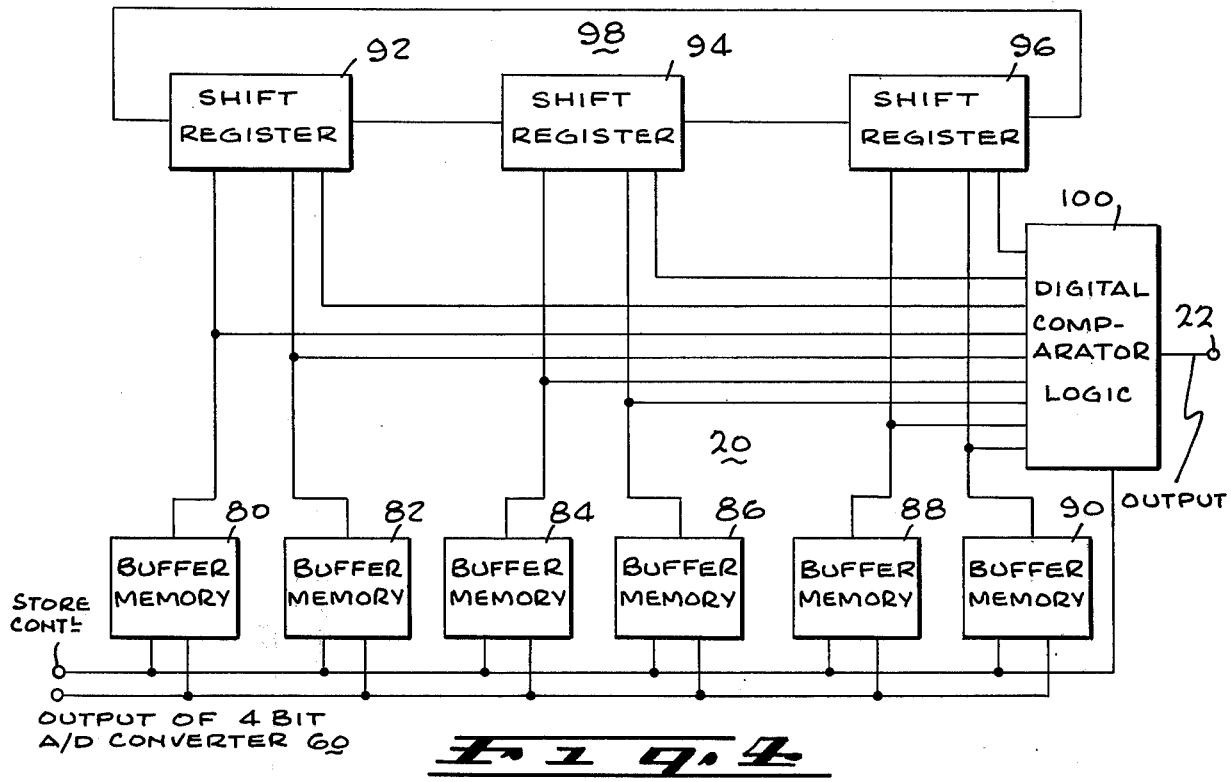
FIG. 4 is a block diagram showing the details of the digital template memory of the arrangement of FIG. 1.

In the present example, the analog to digital converter 18 of FIG. 1 comprises the 4 bit analog to digital converter 60 shown in FIG. 2. The converter 60 is coupled to receive the ECG signal as well as to pass store control signals from the NAND gate 58 to the digital template memory 20. The converter 60 converts the amplitude of each R wave at the six different test points into a corresponding four bit digital value. The four bits corresponding to the amplitude of the R wave at each of the six different test points are temporarily stored in a different one of six different buffer memories 80, 82, 84, 86, 88 and 90 within the digital template memory 20 as shown in FIG. 4. At the end of the six point comparison, the four bit digital values corresponding to the amplitude of the R wave at the six different test points are stored in the buffer memories 80, 82, 84, 86, 88 and 90. If the comparator 50 has determined that the R wave differs from the reference template at at least one of the test points, the R wave is tagged as a potential arrhythmia by generation of the store control signal. The store control signal causes the buffer memories 80, 82, 84, 86, 88 and 90 to apply the digital values to three different shift registers 92, 94 and 96 comprising a recirculating shift register 98 as well as to digital comparator logic 100.

Each of the buffer memories 80, 82, 84, 86, 88 and 90 may comprise an appropriate circuit for storing a four bit word such as a quad latch of the type sold under the designation CD4042 by Radio Corporation of America. In the present example, the shift register 98 has a total capacity of 1056 bits. Since the six sample points of each R wave require twenty-four bits, the shift register 98 has a capacity of 44 R waves. The 44 R wave capacity has been found to be satisfactory in the present example, although registers with other capacities could also be used. On the one hand, the memory must provide enough storage capacity to accommodate the valid arrhythmias together with the considerable amount of noise which is frequently present. On the other hand, memories with an excessive storage capacity tend to be undesirable since there is an increased chance that like noise patterns will repeat, resulting in noise being interpreted as a valid arrhythmia. In the present example, each of the shift registers 92, 94 and 96 may comprise integrated circuits sold under the designation CD4034 by Radio Corporation of America.

As the 44 R wave complexes circulate through the shift registers 92, 94 and 96, each R wave complex is compared with the complex stored in the buffer memories 80, 82, 84, 86, 88 and 90 by the digital comparator logic 100. If a match is found, the digital comparator logic 100 provides an alarm signal to the output terminal 22 indicating an arrhythmia. When the comparison process is terminated, the R wave complex stored in the buffer memories 80, 82, 84, 86, 88 and 90 is transferred in parallel into the shift registers 92, 94, 96 so as to destroy the oldest R wave complex within the shift register 98 while at the same time being itself stored within the register 98. Thereafter, the newly entered R wave complex is circulated within the shift register 98 together with the other 43 stored complexes for comparison with each new potential arrhythmia stored in the buffer memories 80, 82, 84, 86, 88 and 90.

The digital comparator logic 100 may comprise any appropriate conventional circuitry for performing a parallel comparison between 24 bits entered into the buffer memories and groups of 24 bits circulating through the shift register 98. One circuit which may be used in the present example includes adders, two-input and three-input NOR gates and two-input and four-input NOR gates. Commercially available integrated circuits which can be used include those sold by Radio Corporation of America under the designations CD4008, CD4001, CD4025, CD4011 and CD4012.

Figure 5:
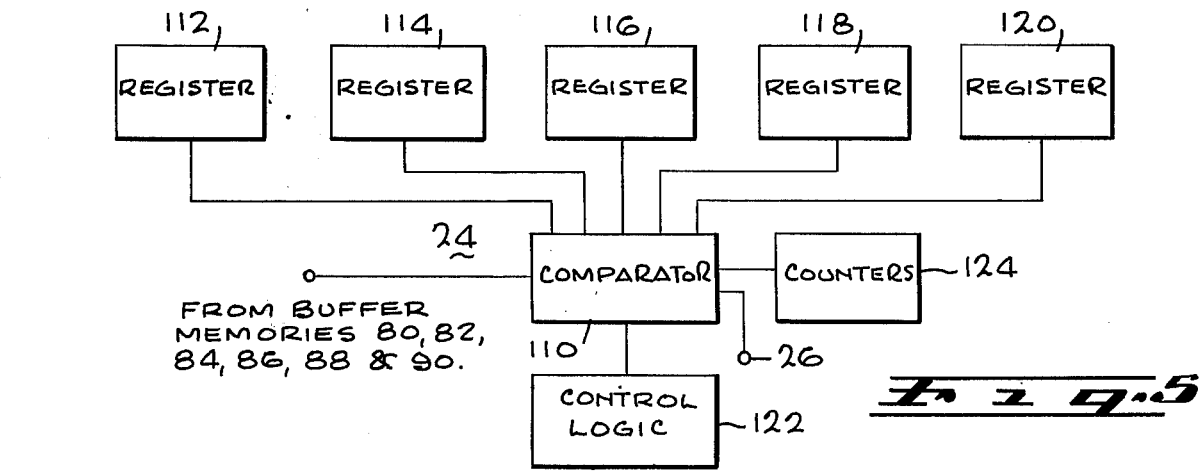
FIG. 5 is a block diagram showing the details of the ectopic beat classifier of the arrangement of FIG. 1.

The ectopic beat classifier 24 of FIG. 1 is shown in detail in FIG. 5. The ectopic beat classifier 24 is an optional circuit which may be added to the arrhythmia detector 10 to further enhance the accuracy of the detector 10. For most applications, the digital template memory 20 provides the necessary noise immunity by identifying R waves which differ from the reference template as arrhythmias only if they are also determined to equal a previously stored R wave of other than the reference form. However, the digital template memory 20 makes no attempt to distinguish between R wave complexes which are shown to be valid arrhythmias by the comparison process and R wave complexes which are not identified as valid arrhythmias, in terms of storing such R wave complexes. As a result, R wave complexes tagged as potential arrhythmias by the self-train morphology template 16 are compared with both valid arrhythmias and stored R wave complexes which are noise produced. As previously noted, noise patterns seldom repeat themselves, thereby enabling the digital template memory 20 to distinguish between noise and valid arrhythmias. However, the possibility always exists that a potential arrhythmia produced by noise will be sufficiently close to previously stored noise complexes, particularly if the comparison tolerances happen to be large enough, so as to result in generation of an arrhythmia alarm signal. The ectopic beat classifier 24 avoids this problem by comparing the potential arrhythmias only with R wave complexes which have been determined to be valid arrhythmias by the digital template memory 20.

When the digital comparator logic 100 determines that a potential arrhythmia stored in the buffer memories 80, 82, 84, 86, 88 and 90 is substantially equal to one of the waveform complexes stored in the shift register 98 so as to denote a valid arrhythmia, the digital bits stored in the buffer memories are passed to a comparator 110 seen in FIG. 5. The comparator 110 is coupled to a plurality of different registers 112, 114, 116, 118 and 120. If the first register 112 is empty, the comparator 110 which operates in response to control logic 122 causes the incoming waveform complex to be stored in the register 112. If the register 112 already has a waveform complex stored therein, the incoming complex is compared with the complex stored in the register 112. If different, the incoming complex is stored in the register 114. If the incoming complex is substantially equal to the complex stored in the register 112, the comparator 110 provides an alarm signal at the output terminal 26 indicating the detection of a valid arrhythmia. The process of comparison and storage continues until all of the registers 112, 114, 116, 118 and 120 are filled with different valid arrhythmias. As noted previously, there are seldom more than a few different valid arrhythmias produced by an abnormal heart. Accordingly, the registers 112, 114, 116, 118 and 120 provide more than enough capacity for most situations. Since the ectopic beat classifier 24 stores only those waveform complexes which have first been determined to be valid arrhythmias, the beat classifier 26 need only be capable of storing a few different complexes rather than many complexes as in the case of the digital template memory 20.

The comparator 110 is also coupled to counters 124. For certain applications, it may be desirable to keep a record of the frequency with which a particular arrhythmia occurs over a given period of time. The counters 124 register a count each time the comparator 110 determines that an incoming wave complex is equal to a complex stored in one of the registers 112, 114, 116, 118 and 120. A different count is maintained for each of the registers. At the end of the given time period, the counters 124 may be looked at to determine the frequency with which each of the wave complexes stored in the various registers occurred.

While the invention has been particularly shown and described with reference to a preferred embodiment thereof, it will be understood by those skilled in the art that various changes in form and details may be made therein without departing from the spirit and scope of the invention.

What is claimed is:

1. A circuit for detecting heart arrhythmias in response to a signal representing the functioning of the heart comprising:

means for storing a plurality of reference values comprising a reference template;

means responsive to the signal representing the functioning of the heart for periodically sampling the signal to provide a plurality of sample values;

means for comparing the sample values with the reference values to provide an alarm signal whenever a difference occurs;

means for averaging the sample values with the reference values to update the reference values; and means responsive to each alarm signal for storing representations of the sample values, and means responsive to each alarm signal for comparing the sample values with the stored representations and operative to provide a second alarm signal whenever the sample values are equal to the stored representations.

2. The invention defined in claim 1, wherein the means for storing representations of the sample values comprises means for converting the sample values into corresponding digital representations, circulating digital register means, and means for storing the digital representations at a selected location within the circulating register means.

3. The invention defined in claim 2, wherein the means for comparing the sample values with the stored representations comprises means for temporarily storing the digital representations of a group of sample values, and means for successively comparing the digital representations with digital representations stored within the dititral register means and representing other groups of sample values.

4. A circuit for detecting heart arrhythmias in response to an electrocardiogram signal comprising:

means responsive to the electrocardiogram signal for generating a timing signal at the beginning of each R wave of the electrocardiogram signal;

means for storing a plurality of reference values defining an R wave template;

means responsive to each timing signal for sequentially comparing a corresponding R wave of the electrocardiogram signal with each of the reference values at a plurality of sample points occurring at different times following the occurrence of the timing signal, the means for sequentially comparing generating a store control signal when at least one of the reference values is detemined not to equal the R wave at a corresponding sample point;

means coupled to the means for storing and responsive to each R wave of the electrocardiogram signal for changing any reference value which is different from the R wave at a corresponding sample point by an amount corresponding to the difference to update the reference value;

means for storing the values at the test points of a plurality of R waves which have been determined by sequential comparing to be different from the reference values at at least one of the test points;

means responsive to each store control signal for comparing a corresponding R wave at each of the test points with the values stored in the means for storing, the means for comparing a corresponding R wave at each of the test points with the values stored in the means for storing being operative to produce an alarm signal when the corresponding R wave is equal to the stored values at each of the test points; and means responsive to each store control signal for storing the values of a corresponding R wave at the test points in the means for storing.

5. The invention defined in claim 4, wherein the means for storing comprises a recirculating shift register.

6. The invention defined in claim 4, further including means responsive to the electrocardiogram signal for generating digital numbers corresponding to the values of the electrocardiogram signal at the test points, and wherein the means for storing stores the values in the form of digital numbers and the means for comparing a corresponding R wave at each of the test points with the values stored in the means for storing compares the digital numbers generated in response to the corresponding R wave at each of the test points with the digital numbers stored in the means for storing.

* * * * *